United States Patent [19]
Knauft et al.

[11] Patent Number: 5,922,390
[45] Date of Patent: Jul. 13, 1999

[54] PEANUT OIL FROM ENHANCED PEANUT PRODUCTS

[75] Inventors: David A. Knauft, Raleigh, N.C.; Daniel W. Gorbet, Marianna, Fla.; Allan J. Norden, deceased, late of High Springs, by Catherine K. Norden; Catherine K. Norden, High Springs, both of Fla.

[73] Assignee: University of Florida Research Foundation, Inc., Gainesville, Fla.

[21] Appl. No.: 08/826,049

[22] Filed: Mar. 28, 1997

Related U.S. Application Data

[62] Division of application No. 08/452,522, May 30, 1995., which is a continuation of application No. 08/272,523, Jul. 11, 1994., abandoned, which is a continuation of application No. 08/177,472, Jan. 5, 1994., abandoned, which is a continuation-in-part of application No. 08/022,434, Feb. 16, 1993., abandoned, which is a continuation-in-part of application No. 07/884,308, May 11, 1992., abandoned, which is a continuation of application No. 07/625,631, Dec. 6, 1990., abandoned, which is a continuation of application No. 07/071,881, Jul. 10, 1987., abandoned

[51] Int. Cl.⁶ .................................................. A23D 9/00
[52] U.S. Cl. ............................ 426/601; 800/200; 554/9
[58] Field of Search ............................ 426/601; 800/200; 554/9

[56] References Cited

U.S. PATENT DOCUMENTS

| | | | |
|---|---|---|---|
| 4,627,192 | 12/1986 | Fick | 47/58 |
| 4,743,402 | 5/1988 | Fick | 260/412.2 |
| 4,948,811 | 8/1990 | Spinner et al. | 514/560 |
| 5,684,232 | 11/1997 | Horn et al. | 800/200 |

OTHER PUBLICATIONS

Peanut Science vol. 14, issue 1, front cover with table of contents and pp. 7–11.
Swern 1979 Baileys Industrial Oil & Fat Products vol. 1 4th ed John Wiley & Sons New York pp. 363–371.
Norden 1987 Peanut Science 14:7–11.
Nordon 1984 Florida Agricultural Research 3 (16–18).
Norden 1986 Oleagineaux 23 (583–585).
Worthington 1971 Oleagineaux 26 (695–700).
Treadwell 1983 Oleagineaux 38 (381–385).
Norden et al, *Oléagineux*, vol. 23, No. 10, "Variety Blends: A Consideration In Peanut Oil Improvement and Production," pp. 583–585 (1968).
Worthington et al, *Oléagineux*, vol. 26, No. 11, "Geno–typic Variation in Fatty Acid Composition and Stability of *Arachis Hypogaea L*. Oil," pp. 695–700 (1971).
Khan et al, *Crop Sci.*, vol. 14, "Refractive Index as a Basis for Assessing Fatty Acid Composition in Segregating Populations Derived from Infraspecific Crosses of Cultivated Peanuts," pp. 464–468 (1974).
Ahmed et al, in *Peanut Science and Technology*, Chapter 17, "Composition, Quality, and Flavor of Peanuts," Patee et al, eds., Am. Peanut Res. Educ. Soc.: Yoakum, TX, pp. 655–688 (1982).

*Primary Examiner*—Carolyn Paden
*Attorney, Agent, or Firm*—Kerkam, Stowell, Kondracki & Clarke, P.C.; Dennis P. Clarke

[57] ABSTRACT

A peanut line and seed and oil products derived therefrom wherein the seed has an oleic acid content of from about 74% to about 84% and a linoleic acid content of from about 2% to about 8%, each based upon the total fatty acid content of the seed, and a ratio of the amount of oleic acid to linoleic acid in the seed of from about 9:1 to about 42:1.

10 Claims, No Drawings

PEANUT OIL FROM ENHANCED PEANUT PRODUCTS

This is a division of application Ser. No. 08/452,522 filed May 30, 1995, which is a continuation of application Ser. No. 08/272,523 filed Jul. 11, 1994 (abandoned), which is a continuation of application Ser. No. 08/177,472 filed Jan. 5, 1994 (abandoned), which is a continuation-in-part of application Ser. No. 08/022,434 filed Feb. 16, 1993 (abandoned), which is a continuation-in-part of application Ser. No. 07/884,308 filed May 11, 1992 (abandoned), which is a continuation of application Ser. No. 07/625,631 filed Dec. 6, 1990 (abandoned), which is a continuation of application Ser. No. 07/071,881 filed Jul. 10, 1987 (abandoned).

BACKGROUND OF THE INVENTION

1. Field of the Invention

The present invention relates to an enhanced peanut plant line and the products derived therefrom.

2. Discussion of the Prior Art

The cultivated peanut (Arachis hypogaea L.) is a self-pollinating annual herbaceous legume characterized by seeds with high oil (45–55%) and protein (25–35%) and a low percentage of carbohydrates and ash. The quality of edible peanuts is due principally to the chemical composition of the oil, protein and carbohydrate fractions of the seeds.

The cultivated peanut originated in South America, along the eastern slopes of the Andes mountains. It now is widely grown and well adapted to tropical, sub-tropical and warm temperate areas of the world. It currently ranks ninth in area among the row crops in the United States and second in dollar value per acre. In the United States, peanuts are utilized primarily as whole seeds and for making peanut butter, while elsewhere in the world they are mainly crushed for oil. Approximately 70% of the world's peanuts are crushed to provide about 20% of the world's vegetable oil. Seeds of the commonly grown cultivars contain 40–52% oil and 25–32% protein.

Since 1928, dramatic improvements have been made in the peanut plant. In the early days of programs, breeders had as their goal the development of a variety that is the best market type and/or also well suited to "hogging off." Today the program must meet the needs of three groups of people: (1) the growers who want a higher yielding variety with more resistance to pests and environmental stresses; (2) the processors who desire more uniform maturity and more favorable processing traits; and (3) the consumer who desires improved nutritional properties, as well as fruit and seeds with preferred shape, size, color, texture and flavor.

Programs have been successful in redesigning the peanut to meet most o these changing needs. The peanut of 40 years ago (Dixie Runner) partitioned only 41% of its assimilate to fruits, while Early Bunch, released in 1977, is an extremely efficient producer of peanuts, partitioning 98% of its assimilate to the fruit. The success of these programs can also be seen in the distribution of varieties, which accounts for approximately 90% of the peanuts produced in the United States. The Florunner variety alone accounted for 71% of the United States peanut acreage in 1982.

Peanut improvement projects generally involve controlled hybridizations followed by pedigreed selection within and between thousands of different lines. The procedure, which spans a period of 10–20 years, is to discard all undesirable plants and lines and to save only those with apparent superiority in economically desirable characteristics. A prerequisite to success is a source of genetic variability and the means of transferring it into the desired variety.

Fortunately, there is a considerable amount of variability available in the cultivated species, especially in morphological and chemical characteristics. The oil content of different genotypes varies from less than 45% to over 55%, and the fatty acid composition of the oil of different lines also shows considerable variability. Some peanut lines have polyunsaturated to saturated oil ratios of almost 2:1, the ratio considered desirable for reduction of blood serum cholesterol. Genetic variability is also available within the species to increase some deficient amino acids, especially methionine, but more variation is needed. More resistance to certain diseases, nematodes, toxin-producing molds and drought is also required.

In some of the wild Arachis species, there is near immunity to rust and Cercospora leafspot disease, as well as spider mite resistance, resistance to lesser cornstalk borer and many other valuable features. However, the wild diploid species (2N=20) are not sexually compatible with the cultivated species where 2N=40. Techniques of embryo rescue, where newly produced embryos are surgically removed and grown in tissue culture and protoplast fusion, which combines cells from different species and attempts to produce whole plants from these vegetative hybrids, may open a vast new gene pool which has, until now, been largely unaccessible to the peanut breeder.

The improvement of peanut oil quality has long been an objective of the successful breeding program since it influences the shelf-life and nutritional quality of manufactured products [Norden, Sunshine State April Res. Report, January, 1968, pages 14–16; and Norden et al, Oleagineaux, Vol. 23, pages 583–585]. Since fatty acids make up the major portion of the weight of an oil molecule, the physical and chemical properties of the oil tend to be determined by the properties of the fatty acids which predominate in their makeup. Although as may as twelve fatty acids have been reported in peanuts, only three are present in amounts exceeding 5%: palmitic, oleic and linoleic [Ahmed et al, Peanut Science and Technology, pages 655–688, Pattee and Young (ed.) (1982)]. These three acids comprise about 90% of the fatty acid composition of the oil, with oleic and linoleic oils comprising about 80%. The remainder of the fatty acids comprise about 10%, each ranging in concentration from 0.02% to 3.59%.

Peanut genotypes are known with as low as 35% and as high as 71% oleic acid and with linoleic acid contents ranging from as low as 11% to as high as 43% [Bovi, Ph.D. Dissertation, University of Florida, page 119 (1982); Treadwell et al, Oleagineaux, Vol. 38, pages 381–385 (1983); Worthington et al, Oleagineaux, Vol. 26, pages 695–700 (1971); Worthington et al, J. Amer. Oil Chem. Soc., Vol. 54, pages 105–108 (1977)]. Studies by Worthington et al (1977), supra, showed that stability of peanut oil and peanut butter samples were highly correlated with levels of linoleic acid, and they concluded that selection for lower levels of linoleic acid in the development of new varieties of peanuts should result in products with significantly improved shelf life.

"Florunner," which is currently the most widely grown commercial peanut cultivar in the United States, has approximately 51% oleic acid and 29% linoleic acid, which results in an oleic acid/linoleic acid (O/L) ratio of slightly less than 2:1.

These two fatty acids dictate the final quality of the peanut product. Oleic acid has one double bond and linoleic acid has two double bonds. The large quantity of linoleic acid partly determines the shelf life of peanuts, i.e, that length of time a peanut product may be stored before becoming rancid. The fewer double bonds present in the oil, the longer the shelf life.

"Sunrunner," another commercially popular market type cultivar, also has a relatively high content of linoleic acid.

Health considerations have made oils with more double bonds (higher unsaturation levels) more desirable as a factor in the reduction of atherosclerosis. Thus, the breeder is faced with the paradox of breeding for more unsaturation for the consumer and less unsaturation for the processor. Recent research in human nutrition has indicated that the high levels of the mono-unsaturated oleic acid is as effective as the polyunsaturated linoleic acid in lowering the blood plasma cholesterol [Mattson et al, J. Lipid Research, Vol. 26, pages 194–202 (1985)]. If peanut lines with higher oleic acid and lower linoleic acid could be developed, such lines would be desired by both the consumer and the processor.

In the parent applications identified above, the entire contents and disclosures of which are incorporated herein by reference, there is described a novel peanut line from which can be derived a novel peanut seed which yields peanut products, in particular oil and food products, having enhanced shelf lives and nutritional qualities because of the high oleic acid and low linoleic acid contents and iodine values thereof. The novel germ-plasm is true-breeding and may also be hybridized with other peanut stocks to produce novel peanut hybrids through selection.

It is an object of the present invention to provide a new peanut plant line for producing peanut seeds which have an unusually high oleic acid content and low linoleic acid level, as well as breeding lines that have substantially the same yield and market grade as existing runner market type cultivars.

It is another object of the present invention to provide a novel peanut product having an enhanced shelf life and high oleic acid content and low linoleic acid level.

SUMMARY OF THE INVENTION

These and other objects are realized by the present invention, one embodiment of which provides a peanut seed having an oleic acid content of from about 74 to about 84% and a linoleic acid content of from about 2% to about 8%, each based upon the total fatty acid content of the seed, and a ratio of the amount of oleic acid to linoleic acid in the seed of from about 9:1 to about 42:1.

The invention further provides a novel peanut plant which produces the above-described seeds.

In addition, the invention provides a peanut seed product consisting essentially of a substantially homogenous assemblage of the above-described peanut seeds.

Further, the invention provides a peanut line consisting essentially of a substantially uniform population of *Arachis hypogaea* L. plants which produce seeds having the above-described characteristics.

The invention also provides a peanut oil and other products having enhanced shelf lives derived from the above-described peanut seeds.

Finally, the invention provides a peanut runner market type cultivar which yields seeds and products having the above-noted characteristics.

DETAILED DESCRIPTION OF THE INVENTION

The novel genotypes were developed according to a modified pedigree system. Standard and modified systems are described in detail in the following references:

Norden, Breeding of the cultivated peanut (*Arachis hypogaea* L.), pages 175–208, in Peanuts, Culture and Uses, Am. Peanut Res. and Educ. Soc., Wilson (ed.), Stillwater, Okla. (1973).

Norden, Peanut, pages 443–456, in Hadley and Fehr (eds.), Hybridization of Crop Plants, Am. Soc. of Agron., Madison, Wis. (1980).

Norden et al, Application genetics in peanut variety improvement, Florida Agr. Res., Vol. 3, pages 16–18 (1984).

The entire disclosures of each of the foregoing references are incorporated herein by reference.

The standard system continues to select single plants through early generations of a cross and combines different plants only when they are approaching genetic uniformity. The present invention is predicated upon bulking and testing at an early stage.

Lines are bulked based on phenotypic similarities, although disease and chemical differences may be great. There are two crucial phases in deciding which sublines should be bulked. Both the vegetative and reproductive characteristics must be considered. By the $F_3$–$F_4$ generation, field and laboratory observations identify which lines can be bulked. From field observations in a given year, it may be determined which lines may or may not bulk before observing the reproductive characteristics. Even then all lines are dug and notes are taken on the fruit and seeds. Disease-free plants with uniform pods and seeds are visually selected. If the entire plot is uniform, it is bulked. If the line is not uniform, but has superior traits, the germ-plast is saved for possible future use. Additional market grade data and results of chemical processing and flavor quality tests are obtained on the bulked lines during the winter. The fruit and seeds of single plant selections are also re-evaluated during the winter. All lines and selections are placed on a table by families.

The present invention includes two specifically preferred novel lines of peanuts, designated UF435-2--1 and UF435-2--2.

The unabbreviated pedigree of these two lines is as follows:

UF 435-2-3-B-2-1-b4-B-B-3-b3-b3-1-B-B
UF 435-2-3-B-2-1-b4-B-B-3-b3-b3-2-B-B

The "UF" in the pedigree represents the University of Florida. The number "435" is the cross number assigned by the University of Florida to the original seed sample received in 1959 from Peanut Investigations, USDA, ARS, CRD, Beltsville, Md. The female parent of cross number 435 is "Florispan," a runner market type (*Arachis hypogaea* L., sub-species *hypogaea*, variety *hypogaea*) and the male parent is a Spanish market type (*Arachis hypogaea* L., sub-species *fastigiata*, variety *vulgaris*).

The first number in the pedigree is the cross number and has reference to the $F_1$ generation. If a capital "B" immediately follows the cross number, it means that this is the reciprocal of the pedigree as listed in the record book of crosses. For example, cross number 427 represents the $F_1$ generation of a cross between ♀ 393-7-1 × ♂ Ga. 119-20 and 427B represents the $F_1$ generation of the reciprocal of this cross or ♀ Ga. 119-20 × ♂ 393-7-1.

Single plant selections and the bulking of single plants form the crux of how the present invention was derived. Each number in the pedigree, following the cross, refers to a specific single plant selection.

EXAMPLE 427B-3-7-1-b3-B3-B

The "3" in this pedigree following 427B refers to the third plant of a series selected in the $F_2$ generation and the "7" refers to the seventh plant of a series selected in the $F_3$ generation.

Bulking of selected plants in indicated in the pedigree by a small letter "b". The small "b" together with the number of single plants bulked is underlined. For example, 427B-3-7-1-b3-B3-B means that three single plants were bulked together in the $F_5$ generation.

Bulking of entire plot or plots is indicated by a large "B" in the pedigree. If more than one plot is bulked, the large "B" together with the number of plots is underlined. For example, 427B-3-7-1-b3-B3-B means that three complete plots (except for very obvious off-type plants) were bulked together in the $F_6$ generation.

Each number or letter in the pedigree after the initial $F_1$ (which is the cross number) represents a generation. When a letter and number are together and underlined, they represent only one generation.

In the case of cross number 435, since the $F_2$ was grown in Beltsville, the generation is actually higher than that obtained from simply counting the numbers and B's on the final pedigree. In other words, $F_{16}$ rather than $F_{15}$.

The basic breeding system used to obtain the two unique UF435 lines is hybridization followed by pedigree selection and is also the breeding system most frequently used by peanut breeders. The $F_1$ generation of the cross and the bulked $F_2$ were grown in Beltsville, Md. In addition to oil quality traits, the 435 material exhibited many variations for many other traits, i.e., plant size and pod and seed shape and size. In the earlier generations, there were many small plants and the pods varied in size from runner market type to very small Spanish market type. In addition, there were many plants with pubescent pods and some with pods too narrow-waisted. In addition, much of the early material carried an undesirable trait, whereby the seed coat and pods often split due to unsynchronized seed and shell development during maturation. Due to the excess seed coat and pod-splitting trait, some of the early lines were found to be more susceptible to infection by the fungus *Asperigillus flavus*. However, in the new high oleic/low linoleic lines of the present invention, the pod and seed coat splitting trait has nearly been eliminated.

The peanut genotypes (lines) selected for fatty acid analysis were grown in accordance with recommended cultural practices. The seeds were planted during the months of April and May, and plants were harvested when judged to be mature based on the general condition of the plants, as well as the color of the seed coat and the inner side of the pod. Irrigation water was applied as needed. Randomly selected samples of unshelled pods were obtained from each genotype, and only sound mature seeds were included.

The fatty acid composition of the total of 494 peanut genotypes from the Florida breeding program (1984 and 1985 crops) was determined and the results of the present invention are set forth below in Table 1. Of the 228 genotypes analyzed from the 1985 season, 118 were from the Marianna, Fla., location and 110 were from the Gainesville, Fla., location. The 298 genotypes from the 1985 crops included 147 from Marianna and 151 from Gainesville. A few cultivars and plant introductions were also included. All of the genotypes had been under experimental observation at the respective locations for several years.

TABLE 1

VARIATION IN OIL QUALITY TRAITS (OLEIC AND LINOLEIC ACIDS, O/L RATIOS AND IODINE VALUE) AMONG SELECTED PEANUT GENOTYPES FROM GAINESVILLE AND MARIANNA (FLORIDA) PLANTINGS IN 1984 AND 1985

| Oil Quality Trait | Level of Concentration of Oil Quality Trait | | | | | |
|---|---|---|---|---|---|---|
| | High | | | Low | | |
| | Lab. No.[a] | Genotype | % | Lab. No.[a] | Genotype | % |
| Oleic | 2-a-8 | UF435-2--1 | 79.91 | 2-a-72 | 631B-16-1- | 36.72 |
| Acid | 2-a-151 | UF435-2--2 | 79.71 | 2-g-35 | 76x4A-3-4- | 36.78 |
| C18:1 | 2-a-119 | 393-7-1- | 66.52 | 2-a-25 | 567A-2-1- | 37.04 |
| | 1-a-14 | NC-FLA-14 | 65.34 | 2-a-46 | 607B-2-4- | 37.13 |
| | 1-a-73 | 427BV-18 | 63.40 | 2-g-103 | 76x16-4-1- | 37.20 |
| | 1-g-90 | 81206 | 63.21 | 2-g-5 | 570A-3-2- | 38.21 |
| | Check[b] | Florunner | 51.07 | | | |
| Linoleic | 2-g-103 | 76x16-4-1- | 43.14 | 2-a-8 | UF435-2--1 | 2.14 |
| Acid | 2-g-35 | 76x4A-3-4- | 42.68 | 2-a-151 | UF435-2--2 | 2.29 |
| C18:2 | 2-a-72 | 631B-16-1- | 42.30 | 1-g-90 | 81206 | 15.28 |
| | 2-g-14 | 76x4A-3-4- | 42.26 | 1-a-14 | NC-FIA-14 | 15.44 |
| | 2-a-46 | 607B-2-4- | 41.40 | 2-a-119 | 393-7-1- | 16.66 |
| | 2-a-25 | 567A-2-1- | 41.34 | 1-g-8 | 76x5-5-2- | 18.59 |
| | Check[b] | Florunner | 29.21 | | | |
| Oleic/Linoleic | 2-a-8 | UF435-2--1 | 37.34 | 2-g-35 | 76x4A-3-4- | 0.861 |
| Acid Ratio | 2-a-151 | UF435-2--2 | 34.81 | 2-g-103 | 76x16-4-1- | 0.862 |
| (O/L) | 1-a-14 | NC-FLA-14 | 4.23 | 2-a-72 | 631B-16-1- | 0.868 |
| | 1-g-90 | 81206 | 4.14 | 2-a-25 | 567A-2-1- | 0.895 |
| | 2-a-119 | 393-7-1- | 3.99 | 2-a-46 | 607B-2-4- | 0.897 |
| | 1-g-8 | 76x5-5-2- | 3.37 | 2-g-5 | 570A-3-2- | 0.931 |
| | Check[b] | Florunner | 1.77 | | | |
| Iodine | 2-g-103 | 76x16-4-1- | 107.64 | 2-a-151 | UF435-2--2 | 73.87 |
| Value | 2-g-14 | 76x4A-3-4- | 106.46 | 2-a-8 | UF435-2--1 | 73.93 |
| | 2-a-72 | 631B-1-6- | 105.61 | 1-g-90 | 81206 | 81.84 |
| | 1-a-86 | 607B-1 | 105.48 | 1-a-14 | NC-FLA-14 | 83.73 |
| | 2-g-140 | 72x38-1-3- | 105.23 | 2-a-90 | 639A-1-9- | 86.52 |

TABLE 1-continued

VARIATION IN OIL QUALITY TRAITS (OLEIC AND LINOLEIC ACIDS, O/L RATIOS AND IODINE VALUE) AMONG SELECTED PEANUT GENOTYPES FROM GAINESVILLE AND MARIANNA (FLORIDA) PLANTINGS IN 1984 AND 1985

| Oil Quality | Level of Concentration of Oil Quality Trait | | | | | |
|---|---|---|---|---|---|---|
| | High | | | Low | | |
| Trait | Lab. No.[a] | Genotype | % | Lab. No.[a] | Genotype | % |
| | 1-g-40 Check[b] | 74x36-6-1-Florunner | 105.19 95.58 | 2-g-80 | 72x94-7-1- | 86.58 |

[a] The first part of the Laboratory number refers to the year the crop was grown (1 = 1984; 2 = 1985); the second part refers to location (a = Gainesville; g = Marianne); and the last part of the number is that assigned to the seed sample in the laboratory.
[b] Oil quality data for the Florunner check is the mean of six samples representing both locations in 1984 and 1985.

Genetic variability, a requisite for varietal improvement, is generally the first concern of plant breeders. Thus, Table 1 includes only the values for the six genotypes having the highest and the six having the lowest levels of the oil quality traits to illustrate the range in variability, along with the values for the commercial cultivar, Florunner.

The dramatic increase of oleic acid and the decrease of linoleic acid, as illustrated by the two UF435 lines of the present invention in Table 1 when compared with Florunner and the known fatty acid composition of all other peanut genotypes is the key to its superiority in stability of the oil and peanut products and in its nutritional quality. The two UF435 lines were developed by selection from a seed sample received in 1959 from a source in Beltsville, Md. In seven earlier years (1968–1974) of oil quality tests, the 435 parental stock had 50.8±1.3% oleic acid and 26.2±1.2% linoleic acid in its oil composition. The iodine value of the oil of UF435 in these seven early years was 91.3±1.3.

The high oleic/low linoleic levels of the peanut lines of the present invention occurred as a result of the method described above, whereby the novel genotypes were developed. There are other crop plants where major genes at one locus change the relative amounts of oleic and linoleic acids. For example, in Safflower oil, high linoleic acid is dominant, but two different alleles give either 75% or 45% oleic acid in homozygous recessives. See Stack et al, Seed Physiology, Vol. 1, pages 209–244, Murray (ed.) (1984). Since oleate is the precursor of both long-chain and polyunsaturated fatty acids, the differences in relative amounts of these fatty acids are presumed to be the result of differences in the relative rates of synthesis and metabolism of oleate.

However, because of its smaller pods and seeds (no pods ride the Virginia 34/64-inch screen and the sound mature seeds weigh 35–45 grams per 100 seeds), it is classified under the U.S. Marketing System as a commercial Spanish type. The seeds of both Florunner and Florispan weigh approximately 60 grams per 100 seeds.

The plants of the new peanut resemble those of Florispan (having a spreading bunch growth habit) and the leaves are somewhat lighter green in color than most other runner market type cultivars. The color difference is more easily noted when grown next to runner market type cultivars.

As discussed previously, the new UF435 genotypes were derived from a seed sample received in 1959. Much of the early material carried an undesirable trait, whereby the seed coat and pods often split due to unsynchronized seed and shell development during maturation. However, in the new high oleic/low linoleic lines of the invention, the pod and seed coat splitting trait has been virtually eliminated. Line UF435-2--1 (85-1237) had 0.8% split pods by weight and line UF435-2--2 (85-1241) had 1.7% split pods, compared with 0.5% split pods for the commonly grown cultivar, "Starr Spanish." The novel peanut of the invention has more uniformly shaped pods than Starr Spanish, having only 8–10% single celled pods by weight, compared with twice this amount or 20% single celled pods for Starr Spanish. Results of fatty acid analysis on the new peanut from the 1986 crop season are substantially the same as those obtained from the 1985 crop.

Preferred lines have an oleic acid content of from about 79 to about 80%, a linoleic acid content of from about 2 to about 3% and an iodine value of from about 73 to about 75. These lines produce seeds having a sound mature weight of from about 35 to about 45 g/100 seeds.

The most preferred lines, however, are those derived from runner market type cultivars. The term "runner market type cultivar" is a term of art well understood by those skilled in this art which refers to runner type cultivars having commercially attractive yields and market grades. The term refers to a type of peanut of the botanical sub-species *hypogaea*, variety *hypogaea*. Cultivars of this sub-species and variety are divided in the United States on the basis of pod size. Those cultivars with ≧40% of pods passing over rollers 13.5 mm apart are classified as Virginia market type cultivars. Those with ≦40% of pods passing over rollers 13.5 mm apart are classified as runner market type cultivars.

Lines of the invention derived from runner market type cultivars produce products having an oleic acid content of from about 74% to about 84%, a linoleic acid content of from about 2% to about 8%, each based upon the total fatty acid content of the product, a ratio of the amount of oleic acid to linoleic acid (O/L) of from about 9:1 to about 42:1, and an iodine value of from about 70 to about 82.

The term "derived" as used herein refers to employing a runner market type cultivar as a recurrent parent and a UF435 line as a donor parent in a backcrossing program to derive the novel runner market type cultivar having the desired characteristics. It is an advantageous feature of the present invention that the novel runner market type cultivars have most of the characteristics of the parent commercial runner type cultivar combined with the high oleic acid content traits of the UF435 line.

The novel runner market type cultivars of the invention were derived from a cross of F435 to a component line of the commercial runner line, e.g., Sunrunner. Sunrunner is a composite of the three breeding lines F519-9, F519-10 and F519-11. Only line F519-9 was used in the backcrossing scheme. The $F_1$ plants were crossed back to the commercial line. The seeds from this cross, which is the first backcross, were planted and the subsequent seeds generated from these plants were analyzed for fatty acid composition. Those seeds with high oleic acid were planted and again crossed to the commercial runner line (the second backcross to Sunrunner). Subsequent growout, seed generation and seed analysis generated plants which were selected to produce those lines identified hereinbelow as F1247 to F1353. The backcrossing was continued a third and a fourth time for generation of the remaining novel lines.

More particularly, in a recently completed program, peanut breeding lines were developed through backcrossing the original high oleic acid line (F435) to a component line (F519-9) of the University of Florida cultivar, Sunrunner. Lines developed from this backcrossing were crossed directly to other lines and cultivars. Segregants from the latter crosses are being handled through pedigree and single seed descent methods to generate new breeding lines.

Backcrossing was carried out with F435 and F519-9 from the initial cross to produce the $F_1$ generation. That $F_1$ was crossed to F519-9 to produce the first backcross generation. After each backcross, self-pollination was allowed to occur to generate the $BC_xF_2$ generations. The individual seeds from each generation were analyzed for fatty acid composition. Those seeds with high oleic acid were planted in the greenhouse for further backcrossing. Seeds were also obtained from these plants for field testing. Field tests were conducted to select desirable plant characteristics, uniformity and high yield potential. From these tests, seven lines were established at the end of the 1990 growing season. These lines were tested for agronomic potential in Gainesville and Quincy (Fla.) in the 1991 growing season. Yield and market grade data for the two locations are listed in Table 2 below.

TABLE 2

YIELD AND MARKET GRADE FOR SEVEN HIGH OLEIC ACID PEANUT BREEDING LINES TESTED IN GAINESVILLE AND QUINCY (FLORIDA) DURING 1991 GROWING SEASON

| 1 | 2 | 3 | 4 | 5 | 6 | 7 | 8 | 9 | 10 | 11 |
|---|---|---|---|---|---|---|---|---|---|---|
| Gainesville Planting ||||||||||||
| F1247 | 3388 | 12.5 | 79.3 | 18.8 | 42.8 | 4.1 | 2.6 | 1.6 | 52.8 | 75.1 |
| F1248 | 3981 | 17.4 | 80.4 | 28.3 | 39.2 | 3.8 | 2.1 | 1.8 | 62.1 | 76.5 |
| F1249 | 3703 | 28.7 | 79.5 | 27.9 | 39.7 | 3.0 | 1.9 | 0.9 | 61.7 | 76.8 |
| F1250 | 3908 | 28.4 | 79.7 | 26.9 | 46.2 | 0.9 | 1.4 | 0.8 | 61.9 | 77.5 |
| F1251 | 3908 | 2.5 | 79.3 | 10.2 | 40.6 | 4.0 | 4.3 | 0.8 | 45.1 | 74.1 |
| F1252 | 3896 | 15.0 | 80.4 | 23.7 | 47.0 | 1.2 | 1.3 | 1.0 | 60.6 | 78.1 |
| F1253 | 3509 | 4.2 | 79.6 | 12.5 | 48.0 | 1.3 | 4.1 | 0.4 | 50.3 | 75.1 |
| Sunrunner | 4138 | 20.1 | 80.3 | 26.6 | 43.6 | 1.8 | 2.2 | 0.3 | 59.8 | 77.8 |
| Florunner | 4525 | 9.6 | 80.9 | 22.4 | 47.6 | 1.4 | 1.9 | 0.6 | 59.1 | 78.4 |
| Quincy Planting ||||||||||||
| F1247 | 3158 | 4.8 | 79.5 | 4.6 |  | 8.5 | 3.5 | — | 49.1 | 76.0 |
| F1248 | 3709 | 4.0 | 81.3 | 11.6 |  | 9.6 | 1.2 | — | 56.5 | 80.1 |
| F1249 | 3624 | 8.7 | 80.6 | 10.4 |  | 7.2 | 0.7 | — | 59.3 | 79.9 |
| F1250 | 3757 | 5.6 | 80.3 | 9.6 |  | 7.3 | 1.2 | — | 58.2 | 79.1 |
| F1251 | 3170 | 0.3 | 80.2 | 2.5 |  | 6.9 | 4.5 | — | 43.2 | 75.7 |
| F1252 | 3436 | 3.6 | 81.0 | 9.8 |  | 5.5 | 0.4 | — | 58.9 | 80.6 |
| F1253 | 3194 | 2.6 | 81.1 | 3.4 |  | 9.5 | 1.8 | — | 53.0 | 79.3 |
| Sunrunner | 3799 | 4.5 | 81.1 | 10.9 |  | 5.3 | 1.3 | — | 54.7 | 79.8 |
| Florunner | 4259 | 0.7 | 81.8 | 6.3 |  | 6.5 | 0.9 | — | 57.3 | 80.8 |
| Marc I | 4320 | — | 79.9 | 2.9 |  | 4.5 | 3.0 | — | 52.1 | 76.9 |

1 = Line; 2 = Yield in lbs./acre; 3 = Virginia pods (proportion of pods riding rollers for Virginia pod classification); 4 = meets (shelling percentage); 5 = proportion of seed classified as extra large kernels; 6 = proportion of seed classified as medium kernels; 7 = sound splits (proportion of seed that split in shelling); 8 = proportion of seed classified as other kernals (sub-standard size); 9 = proportion of seed classified as damaged kernels; 10 = weight in grams of 100 sound, mature seeds; 11 = proportion of seeds that are sound, mature and appropriate size and sound splits.

TABLE 3

MARKET GRADE INFORMATION FOR FORTY HIGH OLEIC ACID BREEDING LINES FORMED AT END OF 1991 GROWING SEASON

| 1 | 2 | 3 | 4 | 5 | 6 | 7 | 8 | 9 | 10 | 11 |
|---|---|---|---|---|---|---|---|---|---|---|
| 1307 | 5.8 | 2.5 | 79.1 | 8.0 | 50.0 | 3.0 | 2.5 | 0.3 | 49.8 | 76.4 |
| 1308 | 5.6 | 6.6 | 78.6 | 10.9 | 51.8 | 1.5 | 2.7 | 0.8 | 48.4 | 75.1 |
| 1309 | 8.5 | 15.8 | 79.5 | 17.3 | 48.8 | 3.3 | 2.2 | 1.1 | 51.2 | 76.2 |
| 1310 | 11.0 | 26.5 | 80.0 | 28.2 | 40.4 | 2.0 | 1.3 | 1.8 | 56.8 | 76.9 |
| 1311 | 5.3 | 23.1 | 80.2 | 24.7 | 44.2 | 2.1 | 2.1 | 0.4 | 55.3 | 77.7 |
| 1312 | 5.0 | 14.2 | 79.3 | 23.0 | 42.1 | 3.6 | 2.3 | 0.6 | 52.8 | 76.4 |
| 1313 | 10.6 | 22.0 | 80.3 | 22.2 | 43.8 | 2.8 | 4.0 | 0.6 | 53.5 | 75.6 |
| 1314 | 7.9 | 17.5 | 79.9 | 15.7 | 50.6 | 2.3 | 3.1 | 0.6 | 53.3 | 76.2 |
| 1315 | 8.0 | 35.4 | 79.8 | 33.6 | 38.6 | 3.0 | 0.7 | — | 59.5 | 79.1 |
| 1316 | 9.2 | 27.0 | 80.1 | 31.5 | 39.9 | 2.0 | 1.8 | 0.3 | 56.2 | 78.0 |
| 1317 | 11.5 | 46.3 | 77.8 | 35.1 | 35.7 | 2.4 | 1.0 | 0.8 | 62.2 | 76.0 |
| 1318 | 7.7 | 38.8 | 79.7 | 36.9 | 36.8 | 2.0 | 0.7 | 0.6 | 64.4 | 78.4 |
| 1319 | 8.4 | 6.7 | 76.2 | 14.5 | 48.2 | 2.5 | 2.1 | 0.4 | 51.7 | 73.7 |
| 1321 | 6.3 | 4.8 | 78.4 | 16.2 | 44.3 | 1.8 | 3.6 | 0.2 | 48.7 | 74.5 |
| 1322 | 5.0 | 0.5 | 78.0 | 7.7 | 50.8 | 2.5 | 2.5 | 0.4 | 41.6 | 75.1 |
| 9999 | 6.0 | 24.5 | 76.9 | 20.9 | 43.5 | 0.6 | 3.5 | 0.1 | 49.7 | 73.3 |
| 8888 | 6.0 | 17.6 | 78.8 | 29.4 | 42.3 | 0.9 | 1.8 | 0.1 | 52.9 | 76.9 |
| 1327 | 5.4 | 1.5 | 76.7 | 15.1 | 45.5 | 0.6 | 5.2 | — | 43.7 | 71.5 |
| 1331 | 3.6 | 10.0 | 80.3 | 31.5 | 41.5 | 2.2 | 1.1 | 1.0 | 53.3 | 78.1 |
| 1332 | 1.3 | 5.7 | 80.0 | 23.5 | 47.9 | 1.1 | 1.6 | 0.1 | 50.6 | 78.3 |
| 1333 | 1.7 | 6.1 | 80.5 | 24.9 | 44.8 | 3.1 | 1.8 | 0.4 | 49.5 | 78.2 |
| 1334 | 1.8 | 6.0 | 80.8 | 24.2 | 42.1 | 4.8 | 2.2 | 0.7 | 49.5 | 77.8 |
| 1335 | 1.2 | 4.2 | 74.0 | 10.1 | 38.6 | 0.8 | 8.9 | 3.0 | 42.5 | 62.8 |
| 1336 | 2.7 | 1.3 | 78.9 | 17.1 | 43.2 | 3.1 | 3.2 | 0.6 | 43.6 | 75.1 |
| 1337 | 3.5 | 1.2 | 79.9 | 26.0 | 41.4 | 3.1 | 2.2 | 1.5 | 46.0 | 76.2 |
| 1338 | 3.9 | 10.9 | 79.3 | 27.2 | 42.7 | 3.6 | 1.2 | 0.6 | 54.2 | 77.4 |
| 1339 | 1.6 | 5.2 | 80.8 | 25.9 | 46.0 | 2.2 | 1.6 | 0.1 | 54.3 | 79.1 |
| 1340 | 2.4 | 3.2 | 80.1 | 30.4 | 43.2 | 1.1 | 1.6 | — | 52.4 | 78.5 |
| 1341 | 1.4 | 4.1 | 79.8 | 22.8 | 38.5 | 4.3 | 2.9 | 1.3 | 49.0 | 75.7 |
| 1342 | 0.1 | 1.1 | 79.8 | 19.1 | 45.0 | 3.6 | 4.2 | 1.9 | 46.7 | 73.8 |
| 1343 | 4.3 | 0.4 | 78.9 | 16.4 | 45.4 | 6.1 | 3.4 | 0.1 | 46.5 | 75.4 |
| 1344 | 4.4 | 6.9 | 78.3 | 30.2 | 38.4 | 4.6 | 2.9 | 0.4 | 55.0 | 74.9 |
| 1345 | 4.1 | 14.4 | 79.6 | 39.0 | 34.1 | 1.7 | 2.2 | 0.5 | 59.5 | 76.9 |
| 1346 | 3.2 | 9.3 | 78.3 | 31.3 | 39.1 | 1.8 | 2.2 | 0.4 | 59.2 | 75.6 |
| 1347 | 2.7 | 11.4 | 79.2 | 30.1 | 39.6 | 1.9 | 2.2 | — | 55.6 | 76.9 |
| 1348 | 2.9 | 9.2 | 80.7 | 33.5 | 40.7 | 0.7 | 1.8 | — | 56.3 | 78.9 |
| 1349 | 4.6 | 9.4 | 79.4 | 31.4 | 41.7 | 1.4 | 2.2 | 0.2 | 57.9 | 77.1 |
| 1351 | 2.8 | 7.0 | 77.9 | 22.3 | 42.7 | 2.4 | 3.5 | 0.6 | 54.5 | 73.8 |
| 1352 | 1.1 | 3.0 | 76.4 | 23.8 | 19.2 | 1.5 | 5.7 | 2.2 | 51.2 | 68.4 |
| 1353 | 1.0 | 1.8 | 71.1 | 8.1 | 29.5 | 1.0 | 15.8 | 6.4 | 41.8 | 48.9 |

1 = Line; 2 = lbs. of seed available; 3 = Virginia pods (proportion of pods riding rollers for Virginia pod classification); 4 = meets (shelling percentage); 5 = proportion of seed classified as extra large kernels; 6 = proportion of seed classified as medium kernels; 7 = sound splits (proportion of seed that split in shelling); 8 = proportion of seed classified as other kernals (sub-standard size); 9 = proportion of seed classified as damaged kernels; 10 = weight in grams of 100 sound, mature seeds; 11 = proportion of seeds that are sound, mature and appropriate size and sound splits.

Table 4 sets forth the iodine values and fatty acid compositions for the lines identified in Table 2 grown in Gainesville, Fla., during the summer of 1991. The number preceding the colon refers to the number of carbon atoms in the fatty acid and the number following the colon refers to the number of unsaturated bonds. Thus, 16:0 is a fatty acid with 16 carbon atoms and no unsaturation (completely saturated). The common names of these fatty acids are as follows:

| | |
|---|---|
| 16:0 | Palmitic acid |
| 18:0 | Stearic acid |
| 18:1 | Oleic acid |
| 13:2 | Linoleic acid |
| 20:0 | Arachidic acid |

TABLE 4

FATTY ACID COMPOSITION

| Line | Iodine Value | 16:0 | 18:0 | 18:1 | 18:2 | 20:0 | 22:0 | 24:0 | 20:1 |
|---|---|---|---|---|---|---|---|---|---|
| F1247 | 74.63 | 6.22 | 2.33 | 80.64 | 2.12 | 1.31 | 2.82 | 1.84 | 2.04 |
| F1248 | 73.89 | 6.67 | 2.91 | 79.33 | 2.39 | 1.61 | 3.28 | 1.87 | 1.94 |
| F1249 | 74.01 | 6.53 | 2.77 | 80.30 | 1.99 | 1.55 | 3.15 | 1.79 | 1.91 |
| F1250 | 77.74 | 6.73 | 2.42 | 77.18 | 5.67 | 1.32 | 2.92 | 1.81 | 1.96 |
| F1251 | 75.41 | 6.17 | 2.43 | 80.13 | 2.77 | 1.36 | 3.00 | 1.98 | 2.16 |
| F1252 | 75.41 | 5.84 | 2.62 | 81.86 | 2.02 | 1.36 | 2.63 | 1.76 | 1.91 |
| F1253 | 76.01 | 6.11 | 2.25 | 80.10 | 3.12 | 1.27 | 2.96 | 2.01 | 2.18 |
| Sunrunner | 92.57 | 9.25 | 2.40 | 55.85 | 25.09 | 1.29 | 2.93 | 1.81 | 1.37 |
| Florunner | 92.04 | 9.62 | 2.56 | 55.04 | 25.18 | 1.33 | 3.03 | 1.84 | 1.39 |

We claim:

1. A peanut oil derived from a peanut seed having an oleic acid content of from about 74% to about 84% and a linoleic acid content of from about 2% to about 8%, each based upon the total fatty acid content of said seed, and a ratio of the amount of oleic acid to linoleic acid in said seed of from about 9:1 to about 42:1.

2. A peanut oil according to claim 1 wherein said linoleic acid content is from about 2% to about 3%.

3. A peanut oil according to claim 1 wherein said oleic acid content is from about 79% to about 80%.

4. A peanut oil according to claim 1, said seed being the product of a peanut plant having the characteristics of a line designated UF435-2--1 or UF435-2--2.

5. A peanut oil according to claim 1, said seed having a sound mature seed weight of from about 35 to about 45 grams per 100 seeds.

6. A peanut oil according to claim 1, said seed having an iodine value of from about 73 to about 75.

7. A peanut oil according to claim 1 which is a product of a runner market type cultivar.

8. A peanut oil according to claim 7 derived from the runner market type cultivar, Sunrunner.

9. A peanut oil according to claim 7, said seed having an iodine value of from about 70 to about 82.

10. A peanut oil according to claim 7, said seed having a sound mature seed weight of from about 45 to about 70 grams per 100 seeds.

* * * * *